United States Patent
Braish et al.

(10) Patent No.: US 6,316,632 B1
(45) Date of Patent: Nov. 13, 2001

(54) PROCESS FOR PREPARING 2-PHENYL-3-AMINOPYRIDINE, SUBSTITUTED PHENYL DERIVATIVES, THEREOF, AND SALTS THEREOF

(75) Inventors: Tamim F. Braish, Ledyard; Stephane Caron, Groton; Michael James Castaldi, Pawcatuck, all of CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/569,010

(22) Filed: May 11, 2000

Related U.S. Application Data

(60) Provisional application No. 60/134,559, filed on May 17, 1999.

(51) Int. Cl.⁷ ............................. C07D 211/72; C07F 5/02
(52) U.S. Cl. ....................... 546/304; 546/308; 546/312; 568/1
(58) Field of Search ................................. 546/304, 309, 546/308, 312; 568/1

(56) References Cited

U.S. PATENT DOCUMENTS

| | | | |
|---|---|---|---|
| 5,232,929 | 8/1993 | Desai | 514/314 |
| 5,364,943 | 11/1994 | Rosei | 546/243 |
| 5,773,450 | 6/1998 | Lowe, III . | |

FOREIGN PATENT DOCUMENTS

| | | |
|---|---|---|
| 9217449 | 10/1992 | (WO) . |
| 9703066 | 1/1997 | (WO) . |
| 9708144 | 3/1997 | (WO) . |
| 9824447 | 6/1998 | (WO) . |
| 9925714 | 5/1999 | (WO) . |

OTHER PUBLICATIONS

Godard et. al., "Convergent Synthesis of the Streptonigrin Alkaloid Skeleton. Directed orthomelation Connection To Aryl–Arl Cross–Coupling", Tetrahedron, vol. 48, No. 20, pp. 4123–4134, 1992.*

Huichang Zhang, et al. Tetrahedron Letters, vol. 37, No. 7, pp. 1043–1044,(1996), "Base Effect on the Cross–coupling of Bulky Arylboronic Acid with Halopyridines".

Stanforth S.P., Tetrahedron, NL, Elsevier Science Publ., Amsterdam,Vol. 54, No. 3–4, pp. 263–303, "Catalytic Cross–Coupling Reactions in Biaryl Synthesis".

Miller, J.A. et al, Tetrahedron Letters, vol. 39, No. 36, pp. 6441–6444, (1998), Preparation of Unsymmetrical Biaryis via Ni– or Pd–Catalyzed Coupling of Aryl Chlorides with Arylzincs.

European Search Report EP 00 30 3889 Aug. 11, 2000.

N. Miyaura, et al. Chem. Rev. (1995) vol. 95, pp 2457–2483, "Palladium–Catalyzed Cross–Coupling Reaction of Organoboron Compounds".

J. A. Miller, et al. Tetrahedron Letters 39 (1998), pp6441–6444, Preparation of Unsymmetrical Biaryls via Ni– or Pd– Catalyzed Coupling of Aryl Chlorides with Arylzincs.

* cited by examiner

Primary Examiner—Alan L. Rotman
Assistant Examiner—Binta Robinson
(74) Attorney, Agent, or Firm—Peter C. Richardson; Paul H. Ginsburg; Seth H. Jacobs

(57) ABSTRACT

A process for preparing 2-phenyl-3-aminopyridine, and substituted phenyl derivatives and salts thereof.

10 Claims, No Drawings

PROCESS FOR PREPARING 2-PHENYL-3-AMINOPYRIDINE, SUBSTITUTED PHENYL DERIVATIVES, THEREOF, AND SALTS THEREOF

This application claims priority under 35 U.S.C. §119(e) from U.S. application Ser. No. 60/134,559, filed May 17, 1999, which application is hereby incorporated by reference herein.

BACKGROUND OF THE INVENTION

The present invention relates to a method for preparing 2-phenyl-3-aminopyridine, its substituted phenyl derivatives, and salts thereof. 2-phenyl-3-aminopyridine and its substituted derivatives are useful in the preparation of compounds that have utility as substance P antagonists.

Substance P is a naturally occurring undecapeptide belonging to the tachykinin family of peptides, members of which exert prompt stimulatory action on smooth muscle tissue. Substance P is a pharmaceutically active neuropeptide that is produced in mammals and possesses a characteristic amino acid sequence that is described in U.S. Pat. No. 4,680,283. The involvement of substance P and other tachykinins in the pathophysiology of numerous diseases has been amply demonstrated in the art. For example, substance P has been shown to be involved in the transmission of pain or migraine, as well as in central nervous system disorders such as anxiety and schizophrenia, in respiratory and inflammatory diseases such as asthma and rheumatoid arthritis, and in gastrointestinal disorders such as ulcerative colitis, irritable bowel syndrome, and Crohn's disease. Tachykinin antagonists have been reported as useful in treating these conditions and in treating cardiovascular diseases, allergic conditions, immunoregulation, vasodilation, bronchospasm, reflex or neuronal control of the viscera, senile dementia of the Alzheimer type, emesis, sunburn, and Helicobacter pylori infection.

A variety of substance P antagonists can be prepared from 2-phenyl-3-aminopyridine. For example, U.S. Pat. No. 5,323,929 describes substance P antagonists of the formula

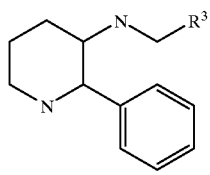

where $R^3$ is a substituted, or unsubstituted aryl, heteroaryl, or cycloalkyl group. These antagonists can be prepared by reduction of 2-phenyl-3-aminopyridine, followed by reductive amination of the resulting 2-phenyl-3-aminopiperidine using an appropriate aldehyde of the formula $R^3CHO$. Alternately, these substance P antagonists can be obtained by reacting 2-phenyl-3-aminopyridine with a compound of the formula $R^3CHO$ or $R^3CH_2X$, where X is a leaving group, to produce the pyridine analog of the substance P antagonist. The pyridine analog is then reduced to obtain the final product.

Additional substance P antagonists that can be prepared from 2-phenyl-3-aminopyridine are described in U.S. Pat. No. 5,773,450, and in WO 97/08144 and PCT/IB97/01466. Methods employing 2-phenyl-3-aminopyridine to make substance P antagonists are also described in U.S. Pat. No. 5,232,929.

However, the conventional method employed to prepare 2-phenyl-3-aminopyridine, described by Miller and Farrell (Tetrahedron Letters, 1998, 39: 6441–6444) is air sensitive and results in a relatively low yield.

SUMMARY OF THE INVENTION

The present invention relates to a process for preparing 2-phenyl-3-aminopyridine substituted phenyl derivatives thereof, and salts thereof. In one aspect, the invention comprises reacting a compound of the formula

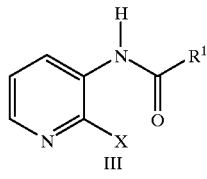

III or

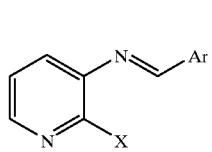

VIII with a compound of the formula

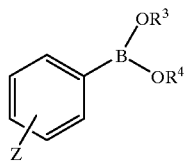

IV in a reaction inert solvent in the presence of a base and a palladium catalyst to obtain a compound of the formula

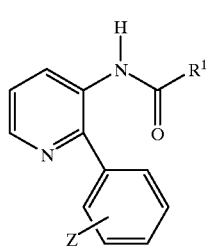

V or

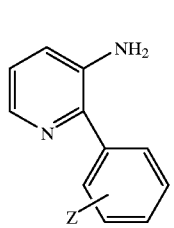

X wherein:
X is Cl, Br, or I;
Z is H, $(C_1-C_4)$ alkyl, methoxy, trifluoromethoxy, F, or Cl;
Ar is $(C_6-C_{10})$ aryl optionally substituted by from 1 to 3 $R^5$ groups;
$R^1$ is $(C_1-C_6)$ straight or branched alkyl, $(C_3-C_7)$ cycloalkyl, or $(C_6-C_{10})$ aryl, said alkyl, cycloalkyl, and aryl groups beings optionally substituted by from 1 to 3 $R^5$ groups;

$R^3$ and $R^4$ are independently selected from H, and $(C_1-C_6)$ alkyl, wherein when $R^3$ and $R^4$ are $(C_1-C_6)$ alkyl they may be fused together to form a ring structure; and each $R^5$ is independently selected from halo, cyano, nitro, $(C_1-C_6)$ halosubstituted alkyl, $(C_1-C_6)$ alkoxy, $(C_6-C_{10})$ aryloxy, $(C_1-C_6)$ halosubstituted alkoxy, $(C_1-C_6)$ alkyl, $(C_2-C_6)$ alkenyl, $(C_2-C_6)$ alkynyl, $(C_1-C_6)$ alkylthio, $(C_1-C_6)$ alkylsulfinyl, $(C_1-C_6)$ alkylsulfonyl, $(C_1-C_6)$ alkyl-OC(O)—, $(C_1-C_6)$ alkyl-OC(O)—$(C_1-C_6)$ alkyl-, $(C_1-C_6)$ alkyl-C(O)O—, $(C_1-C_6)$ alkyl-C(O)—$(C_1-C_6)$ alkyl-O—, $(C_1-C_6)$ alkyl-C(O)—, $(C_1-C_6)$ alkyl-C(O)—$(C_1-C_6)$ alkyl-, $(C_6-C_{10})$ aryl-, $(C_6-C_{10})$ aryl-$(C_1-C_6)$ alkyl-, and $(C_3-C_7)$ cycloalkyl wherein one or two of the carbon atoms of said cycloalkyl may optionally be replaced by nitrogen, oxygen, or sulfur.

In a preferred embodiment, the compound of formula III or VII is prepared by reacting a compound of the formula

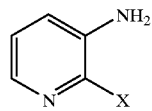

I with a compound of the formula

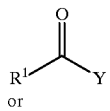

II or

ArCHO

VII in a reaction inert solvent,
wherein:
Y is Cl, Br, I, or —C(O)R²;
and $R^2$ $(C_1-C_6)$ is straight or branched alkyl, $(C_3-C_7)$ cycloalkyl, or $(C_6-C_{10})$ aryl, said alkyl, cycloalkyl, and aryl groups beings optionally substituted by from 1 to 3 $R^5$ groups, wherein said reaction of compound III or VIII with compound IV occurs substantially simultaneously with, or subsequent to, said reaction of compound I with compound II or VII.

The compound of formula V is preferably deprotected in aqueous acid to obtain a salt of compound X.

In one aspect of the above-described method, the invention involves the steps of:

(a) reacting a compound of the formula

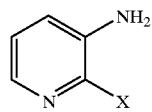

I with a compound of the formula

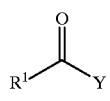

II in a reaction inert solvent in the presence of a base to obtain a compound of the formula

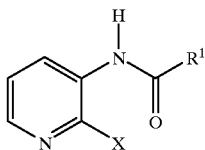

III (b) reacting the compound of formula III with a compound of the formula

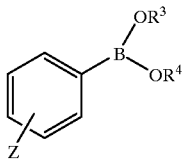

IV in a reaction inert solvent in the presence of a base and a palladium catalyst to obtain a compound of the formula

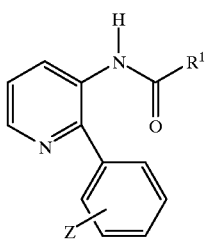

V and
(c) deprotecting the compound of formula V in aqueous acid to obtain a salt of a compound of the formula

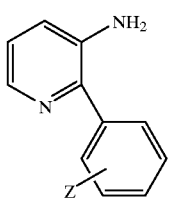

X wherein:
X, Y, Z, $R^1$, $R^2$, $R^3$, $R^4$, and $R^5$ are defined as described above. In another aspect of the above described method, the invention involves the steps of (a) reacting a compound of the formula

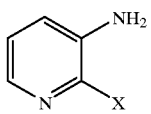

I with a compound of the formula ARCHO VII
in a reaction inert solvent to obtain a compound of the formula

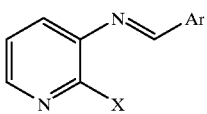

VIII and (b) substantially simultaneously with, or subsequent to, step (a), reacting the compound of formula VIII with a compound of the formula

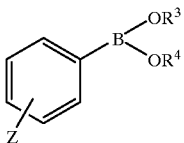

in a reaction inert solvent in the presence of a base and a palladium catalyst to obtain a compound of the formula

X

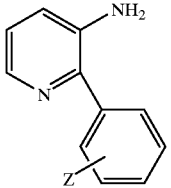

wherein step (a) is further conducted in the presence of a base where steps (a) and (b) are conducted substantially simultaneously,
and wherein Ar, X, Z, $R^3$, $R^4$, and $R^5$ are defined as described above.

In preferred embodiments of the invention, X is Cl, Z is H, and, where relevant, Y is Cl.

In a preferred embodiment, Ar is selected from phenyl and naphthyl optionally substituted by from 1 to 3 $R^5$ groups.

In other embodiments of the invention, $R^1$ and $R^2$ are the same, and preferably are both methyl.

In other embodiments, $R^1$ is methyl and $R^2$ is t-butyl.

In another embodiment, $R^1$ and $R^2$ are independently selected from ($C_1$–$C_6$) straight or branched alkyl, and phenyl.

In a further preferred embodiment, $R^3$ and $R^4$ are H.

In another preferred embodiment, each $R^5$ is independently selected from ($C_1$–$C_6$) straight or branched alkyl, phenyl, benzyl, trifluoromethyl, ($C_1$–$C_6$) alkoxy, F, Cl, and trifluoromethoxy.

In a further preferred embodiment, Z is H; $R^1$ and $R^2$ are the same, are independently selected from ($C_1$–$C_6$) straight or branched alkyl, and phenyl, and are optionally substituted by from 1 to 3 $R^5$ groups; $R^3$ and $R^4$ are H; and each $R^5$ is independently selected from ($C_1$–$C_6$) straight or branched alkyl, phenyl, benzyl, trifluoromethyl, ($C_1$–$C_6$) alkoxy, and trifluoromethoxy.

The term "alkyl" is used herein, unless otherwise indicated, to refer to a saturated monovalent hydrocarbon radical, including, but not limited to, methyl, ethyl, n-propyl, isopropyl, n-butyl, isobutyl, and t-butyl.

The term "alkenyl" is used herein, unless otherwise indicated, to refer to a monovalent hydrocarbon radical having at least one carbon-carbon double bond, including but not limited to, vinyl, 1-propenyl, allyl, isopropenyl, 1-butenyl, 2-butenyl, 3-butenyl, 1,3-butadienyl, and encompassing E and Z isomers of such alkenyl radicals.

The term "alkynyl" is used herein, unless otherwise indicated, to refer to a monovalent hydrocarbon radical having at least one carbon-carbon triple bond, including but not limited to, ethynyl, 2-propynyl, and 3-butynyl.

The term "aryl" is used herein, unless otherwise indicated, to refer to an aromatic radical including, but not limited to, phenyl, naphthyl, pyridyl, quinolyl, thienyl, furyl, oxazolyl, tetrazolyl, thiazolyl, imidazolyl, and pyrazolyl.

The term "alkoxy" is used herein, unless otherwise indicated, to refer to an —O-alkyl radical including, but not limited to, methoxy, ethoxy, propoxy, isopropoxy, n-butoxy, isobutoxy, and t-butoxy.

The term "halo" is used herein, unless otherwise indicated, to refer to a radical derived from the elements fluorine, chlorine, bromine or iodine.

The term "halosubstituted alkyl" is used herein, unless otherwise indicated, to refer to an alkyl radical substituted with one or more halogens including, but not limited to, chloromethyl, difluoromethyl, trifluoromethyl, and 2,2,2-trichloroethyl.

The term "halosubstituted alkoxy" is used herein, unless otherwise indicated, to refer to an alkoxy radical substituted with one or more halogens including, but not limited to, chloromethoxy, difluoromethoxy, trifluoromethoxy, and 2,2,2-trichloroethoxy.

The term "alkylthio" is used herein, unless otherwise indicated, to refer to an -S-alkyl radical including, but not limited to, methylthio, ethylthio, n-propylthio, isopropylthio, n-butylthio, isobutylthio, and t-butylthio.

The term "alkylsulfinyl" is used herein, unless otherwise indicated, to refer to an —SO-alkyl radical, including, but not limited to, methylsulfinyl, ethylsulfinyl, and isopropylsulfinyl.

The term "alkylsulfonyl" is used herein, unless otherwise indicated, to refer to an —$SO_2$-alkyl radical, including, but not limited to, methylsulfonyl, ethylsulfonyl, and isopropylsulfonyl.

DETAILED DESCRIPTION OF THE INVENTION

All publications, patents, and patent applications cited in the present application are hereby incorporated by reference in their entireties.

The method of the invention is capable of obtaining 2-phenyl-3-aminopyridine, and its substituted derivatives, in a higher yield than that obtained using the conventional method, and is less air sensitive.

The preparation of 2-phenyl-3-aminopyridine according to the invention is illustrated by the following reaction schemes.

Scheme 1

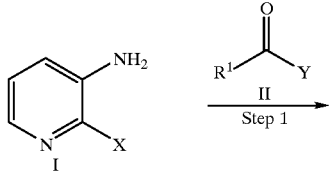

-continued

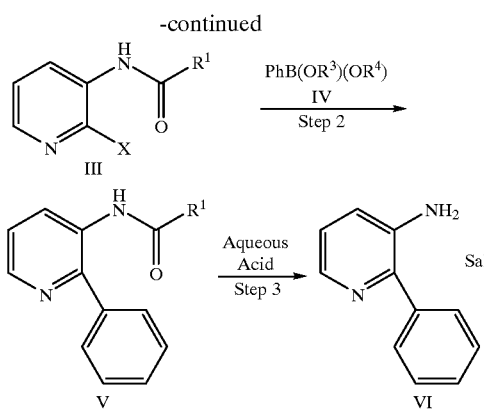

Scheme 2

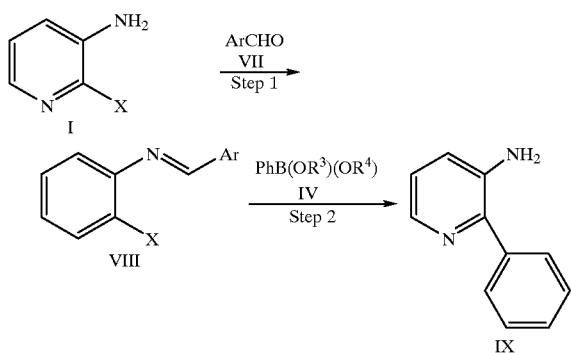

Scheme 3

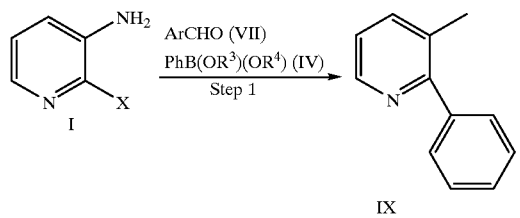

Step 1 of Scheme 1 involves the protection of compound I. In particular, compound I is reacted with an acylating agent of formula II in the presence of a base and a reaction inert solvent at a temperature of between −20° C. and 60° C. for a period of from 1 hour to 48 hours to obtain the acylated aniline compound of formula III. Suitable bases include but are not limited to triethylamine, diisopropylethylamine, 2,6-lutidine, N,N,N',N'-tetramethylethylenediamine, potassium carbonate, sodium hydroxide, and potassium hydroxide. Suitable reaction inert solvents include but are not limited to dichloromethane, dichloroethane, and toluene. For example, in one embodiment, step 1 of Scheme 1 is carried out in the presence of triethylamine and dichloromethane at a temperature of between 0° C. and room temperature, for a period of about 14 hours.

Step 2 of Scheme 1 involves a Suzuki coupling (Miyaura et al. *Chem. Rev.* 1995, 95: 2457) between the compound of formula III and the compound of formula IV to obtain the biaryl of formula V. Step 2 is carried out in a reaction inert solvent in the presence of a base and a palladium catalyst at a temperature of between room temperature and 125° C. for a period of between 30 minutes to 48 hours, to obtain the compound of formula V. Suitable bases include but are not limited to sodium carbonate, sodium bicarbonate, potassium carbonate, potassium hydroxide, sodium hydroxide, potassium fluoride, and barium hydroxide. Suitable palladium catalysts include but are not limited to tetrakis(triphenylphosphine)palladium(0), dichlorobis(triphenylphosphine)palladium(II), palladium(II) acetate, allylpalladium chloride dimer, and tris(dibenzylideneacetone)dipalladium(0). The reaction medium may optionally also contain a tri($C_6$–$C_{10}$) arylphosphine or tri($C_1$–$C_6$) alkylphosphine, examples of which include but are not limited to triphenylphosphine, tri-tert-butylphosphine, and tri-o-tolylphosphine. Suitable reaction inert solvents include but are not limited to tetrahydrofuran, toluene, dioxane, dimethoxyethane, ethanol, dimethylformamide, and dimethylacetamide, optionally containing water. For example, in one embodiment, step 2 of scheme 1 is carried out by reacting a compound of formula III with phenylboronic acid in the presence of sodium carbonate and the palladium catalyst tetrakis(triphenylphosphine)palladium (0), in a mixture of toluene, ethanol, and water, at a temperature of about 100° C. for a period of about 8 hours.

Step 3 of Scheme 1 involves the deprotection of compound V. In particular, the acylated aniline of compound V is reacted with an aqueous acid for a period of from 1 to 48 hours at a temperature between room temperature and reflux, to obtain a salt of 2-phenyl-3-aminopyridine (compound VI). Suitable acids include but are not limited to hydrochloric acid, hydrobromic acid, sulfuric acid and trifluoroacetic acid. For example, in one embodiment, step 3 is carried out in hydrochloric acid at reflux temperature for about 14 hours to obtain a hydrochloride salt of 2-phenyl-3-aminopyridine.

Step 1 of Scheme 2 involves the formation of an imine. The aniline compound of formula I is treated with the aldehyde compound of formula VII, in a reaction inert solvent using a dehydrating agent or apparatus at a temperature between room temperature and reflux for a period of between 4 hours and 48 hours to afford a compound of formula VII. Suitable reaction inert solvents include but are not limited to toluene, xylene, tetrahydrofuran, heptane, dioxan, and dimethoxyethane. Suitable dehydrating agents include but are not limited to magnesium sulfate, titanium tetrachloride, and sodium sulfate; alternately, a Dean-5 Stark apparatus may be used. For example, in one embodiment the compound of formula 1 is reacted with the compound of formula VII in toluene for about 18 hours, employing a Dean-Stark apparatus, to obtain the compound of formula VIII.

Step 2 of Scheme 2 involves a Suzuki coupling between the compound of formula VII and the compound of formula IV to obtain 2-phenyl-3-aminopyridine (formula IX). In particular, the compound of formula VII is treated with the compound of formula IV in a reaction inert solvent optionally containing water, in the presence of a base and a palladium catalyst at a temperature of between room temperature and 125° C. for a period of between 10 minutes and 24 hours to obtain 2-phenyl-3-aminopyridine (formula IX). Suitable bases include but are not limited to sodium carbonate, sodium bicarbonate, potassium carbonate, potassium hydroxide, sodium hydroxide, and barium hydroxide. Suitable palladium catalysts include but are not limited to tetrakis(triphenylphosphine)palladium(0), dichlorobis(triphenylphosphine)palladium(II), palladium(II) acetate, allylpalladium chloride dimer, and tris(dibenzylideneacetone)dipalladium(0). The reaction medium may optionally also contain a tri($C_6$–$C_{10}$) arylphosphine or tri($C_1$–$C_6$) alkylphosphine, examples of which include but are not limited to triphenylphosphine, tri-tert-butylphosphine and tri-o-tolylphosphine. Suitable solvents include but are not limited to tetrahydrofuran, toluene, dioxane, dimethoxyethane, ethanol, dimethylformamide, and dimethylacetamide. For example, in one embodiment, the compound of formula VII is reacted with phenylboronic acid in the presence of sodium carbonate and tetrakis (triphenylphosphine)palladium(0) in a mixture of toluene and water at a temperature of about 100° C. for about 30 minutes to obtain 2-phenyl-3-aminopyridine.

Scheme 3 involves an embodiment of the present invention similar to the method of Scheme 2 but which proceeds through in situ protection of the aniline compound of formula I, i.e., the steps of forming a protected compound, and coupling that compound with a phenyl group, as in steps 1 and 2 of Scheme 2, occur substantially simultaneously. Specifically, in Scheme 3 compound I is treated with an aldehyde of formula VII and a compound of formula IV in a reaction inert solvent in the presence of a base and a palladium catalyst at a temperature between room temperature and 125° C. for a period of between 10 minutes and 48 hours to provide 2-phenyl-3-aminopyridine (formula IX). Suitable bases include but are not limited to sodium hydroxide, sodium carbonate, sodium bicarbonate, potassium carbonate, potassium hydroxide, and barium hydroxide. Suitable palladium catalysts include but are not limited to palladium(II) acetate, tetrakis(triphenylphosphine) palladium(0), dichlorobis(triphenylphosphine)palladium (II), allylpalladium chloride dimer, and tris (dibenzylideneacetone)dipalladium(0). The reaction medium may optionally also contain a tri($C_6$–$C_{10}$) arylphosphine or tri($C_1$–$C_6$) alkylphosphine, examples of which include but are not limited to triphenylphosphine, tri-tert-butylphosphine and tri-o-tolylphosphine. Suitable reaction inert solvents include but are not limited to toluene, tetrahydrofuran, dioxane, dimethoxyethane, ethanol, dimethylformamide, and dimethylacetamide. The reaction medium may also contain water. For example, in one embodiment, the compound of formula I is treated with the compound of formula VII and phenylboronic acid in the presence of sodium hydroxide and palladium(II) acetate and triphenylphosphine, in a mixture of toluene and water at a temperature of about 100° C. for a period of about 18 hours to obtain 2-phenyl-3-aminopyridine.

Derivatives of 2-phenyl-3-aminopyridine wherein the phenyl group is substituted with Z, as defined above, and Z is other than H, are obtained by employing the corresponding compound of the formula

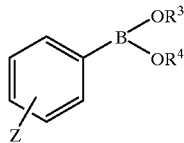

in place of

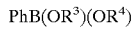

PhB($OR^3$)($OR^4$)

in the reaction schemes shown.

2-phenyl-3-aminopyridine can be converted into substance P-antagonists by following methods described in U.S. Pat. Nos. 5,323,929; 5,232,929; 5,773,450; and in WO 97/08144 and PCT/IB97/01466.

The substance P-antagonists formed thereby are capable of forming a wide variety of salts with various inorganic and organic acids. Although such salts must be pharmaceutically acceptable for administration to animals, it is often desirable in practice to initially isolate the base compound from the reaction mixture as a pharmaceutically unacceptable salt, then convert it to the free base compound by treatment with an alkaline reagent and thereafter convert the free base to a pharmaceutically acceptable acid addition salt. The acid addition salts are readily prepared by treating the base compound with a substantially equivalent amount of the chosen mineral or organic acid in an aqueous solvent or in a suitable organic solvent, such as methanol or ethanol. Upon evaporation of the solvent, the desired solid salt is obtained. The acids which are used to prepare the pharmaceutically acceptable acid addition salts of the base compounds are those which form non-toxic acid addition salts, i.e., salts containing pharmaceutically acceptable anions, such as hydrochloride, hydrobromide, hydroiodide, nitrate, sulfate or bisulfate, phosphate or acid phosphate, acetate, lactate, citrate or acid citrate, tartrate or bi-tartrate, succinate, maleate, fumarate, gluconate, saccharate, benzoate, methanesulfonate, ethanesulfonate, benzenesulfonate, p-toluenesulfonate and pamoate (i.e., 1.1'-methylene-bis-(2-hydroxy-3-naphthoate)) salts.

The substance P antagonists formed using 2-phenyl-3-aminopyridine as an intermediate exhibit significant substance P receptor-binding activity and therefore are of value in the treatment of a wide variety of clinical conditions which are characterized by an excess of substance P activity. Such conditions include, but are not limited to, cardiovascular diseases, allergic disorders, angiogenesis, gastrointestinal disorders, central nervous system disorders, inflammatory diseases, emesis, urinary incontinence, pain, migraine, severe anxiety disorders, stress disorders, anxiety, major depressive disorders, major depressive go disorders with anxiety, depression, sunburn, sexual dysfunction, bipolar disorders, substance use disorders, schizophrenic disorders, movement disorders, cognitive disorders, and diseases, disorders and adverse conditions caused by *Helicobacter pylori,* in a mammal, especially humans. For treatment of emesis, these compounds may be used in combination with a $5HT_3$ receptor antagonist.

The substance P-antagonists, or their pharmaceutically acceptable salts, can be administered via the oral, parenteral (e.g., intravenous, intramuscular or subcutaneous), or topical routes to mammals. In general, these compounds are most desirably administered to humans in doses ranging from 0.3 mg up to 750 mg per day, although variations will necessarily occur depending upon the weight and condition of the subject being treated and the particular route of administration. However, a dosage that is in the range of from 0.06 mg to 6 mg per kg of body weight per day is most desirable.

The substance P-antagonists may be administered alone or in combination with pharmaceutically acceptable carriers or diluents by any of the routes described above, and in single or multiple doses. Thus, the substance P-antagonists can be administered in a wide variety of dosage forms, including tablets, capsules, lozenges, troches, hard candies, powders, sprays, creams, salves, suppositories, jellies, gels, pastes, lotions, ointments, aqueous suspensions, injectable solutions, elixirs, and syrups. Suitable pharmaceutically acceptable carriers for use in such dosage forms include solid diluents or fillers, sterile aqueous media, and various nontoxic organic solvents. Oral pharmaceutical compositions can be suitably sweetened and/or flavored. In general, the substance P antagonists are present in such dosage forms at concentration levels ranging from 5.0% to 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders such as polyvinylpyrrolidone, sucrose, gelatin and acacia. In addition, lubricating agents such as magnesium stearate, sodium lauryl sulfate and talc can be used for tabletting. Similar compositions may also be employed as fillers in gelatine capsules; preferred materials include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if desired, emulsifying and/or suspending agents together with diluents such as water, ethanol, propylene glycol, and glycerin.

For parenteral administration, solutions of the substance P antagonist in either sesame or peanut oil or in aqueous propylene glycol may be employed. Aqueous solutions should be suitably buffered (preferably pH>8) if necessary and the liquid diluent first rendered isotonic. Such aqueous solutions are suitable for intravenous injection. Oily solutions are suitable for intra-articular, intramuscular and subcutaneous injection. The preparation of these solutions under sterile conditions is readily accomplished by standard pharmaceutical techniques.

The present invention is illustrated by the following examples, but is not limited to the details thereof.

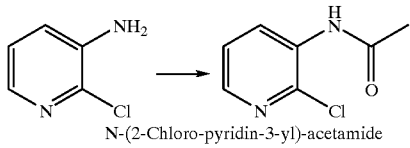
N-(2-Chloro-pyridin-3-yl)-acetamide

To a solution of 2chloro-3-aminopyridine (51.4 g, 400 mmol) in dichloromethane (800 mL) at 0° C. was added triethylamine (31.0 mL, 440 mmol) followed by acetyl chloride (62.0 mL, 440 mmol). The reaction was allowed to warm to room temperature and was stirred overnight. The reaction mixture was poured into water (800 mL) and the layers were separated. The organic layer was treated with Darco™-G-60 (activated charcoal), heated to reflux, filtered over Celite™ (diatomaceous earth manufactured by Celite Corp., Santa Barbara, Calif.) and concentrated to an oil. The oil was crystallized in diisopropyl ether and the solids were filtered to afford 42.4 g (62% yield) of N-(2-chloro-pyridin-3-yl)-acetamide. M. p.=81–83° C. $^1$ NMR (400 MHz, CDCl$_3$) δ2.23 (s, 3), 7.21 (dd, 1, J=8.1, 4.7) 7.67 (bs, 1), 8.06 (dd, 1, J=4.7, 1.3), δ8.66 (d, 1, J=7.9). $^{13}$C NMR (100 MHz, CDCl$_3$) δ24.93, 123.34, 129.06, 131.89, 143.81, 144.08, 168.79.

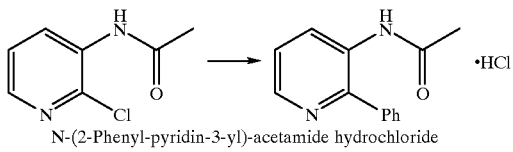
N-(2-Phenyl-pyridin-3-yl)-acetamide hydrochloride

To a mixture of N-(2-chloro-pyridin-3-yl)-acetamide (50,0 g, 29.3 mmol), phenylboronic acid (39.3 g, 32.2 mmol), sodium carbonate (49.7 g, 46.9 mmol), in toluene (400 mL), ethanol (100 mL), and water (200 mL) was added tetrakis(triphenylphosphine)palladium(0) (1.02 g, 0.883 mmol). The reaction mixture was heated to reflux for 8 hours, cooled to room temperature, and the layers were separated. The aqueous layer was extracted with ethyl acetate (500 mL) and the organic extracts were combined and concentrated to a yellow solid. The crude solid was dissolved in methanol (500 mL) and concentrated hydrochloric acid was added (10 mL). The solution was concentrated to a low volume and tetrahydrofuran (500 mL) was added. The solid was triturated, filtered and dried to afford N-(2-phenyl-pyridin-3-yl)-acetamide hydrochloride (62.5 g, 86%). M. p.=262–263° C. $^1$H NMR (300 MHz, DMSO$_{d6}$) δ2.52 (s, 3), 6.30 (bs, 2), 7.64–7.72 (m, 6), 7.78 (dd, 1, J=1.2, 8.6), 8.06 (dd, 1, J=1.2, 5.2)

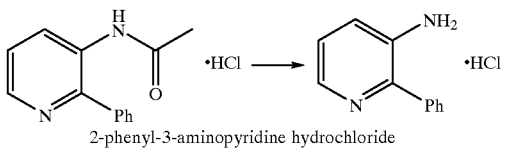
2-phenyl-3-aminopyridine hydrochloride

To a solution of N-(2-phenyl-pyridin-3-yl)-acetamide hydrochloride (61.9 g, 24.9 mmol) in tetrahydrofuran (100 mL) was added concentrated hydrochloric acid (100 mL). The reaction mixture was heated to reflux overnight and concentrated to a low volume. Tetrahydrofuran was added (2000 mL) and the volume was reduced to about 1000 mL as, product started precipitating. The mixture was cooled to 0° C. and was granulated for two) hours. The solids were filtered to afford 2-phenyl-3-aminopyridine hydrochloride (46.2 g, 90%). M. p.=226–1227° C. $^1$H NMR (300 MHz, CDCl$_3$) δ6.35 (bs, 3), 7.61–7.74 (m, 6), 7.82 (dd, 1, J=1.4, 8.6), 8.05 (dd, 1, J=1.5, 5.4). Analysis calculated for C$_{11}$H$_{11}$ClN$_2$: C, 63.93; H, 5.36; N, 13.55. Found: C, 63.64; H, 5.20; N, 13.49.

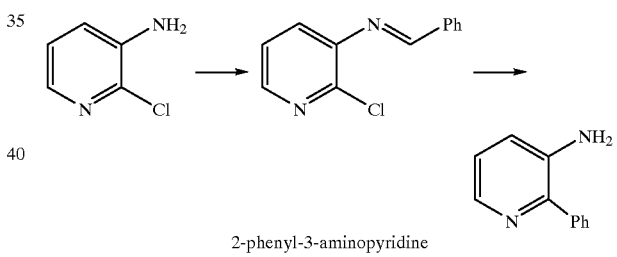
2-phenyl-3-aminopyridine

To 2-chloro-3-aminopyridine (1.06 g, 8.24 mmol) in toluene (25 mL) was added benzaldehyde (0.878 g, 8.27 mmol). The reaction mixture was stirred at reflux in a Dean-Stark apparatus until GC/MS analysis of the reaction mixture no longer showed starting material. The reaction mixture was cooled to room temperature and the toluene solution containing benzylidene-(2-chloro-pyridin-3-yl)-amine was added to a mixture of phenylboronic acid (1.30 g, 10.7 mmol), sodium carbonate (2.66 g, 25.1 mmol), and tetrakis(triphenylphosphine)palladium(0) (47 mg, 0.38mol %) in water (10 mL). The reaction mixture was heated to 100° C. for 30 minutes, cooled to room temperature and poured into 1N aqueous sodium hydroxide (10 mL). The aqueous layer was removed and the toluene layer was extracted with 1N aqueous hydrochloric acid (twice with 15 mL). The aqueous layer was neutralized to pH 12 with 6N aqueous sodium hydroxide and extracted with MTBE (twice with 20 mL). The MTBE extracts were dried over magnesium sulfate, filtered and concentrated to afford 2-phenyl-3-aminopyridine as a solid which crystallized from diisopropyl ether (1.26 g, 90% yield). M. p.=87–68° C. $^1$H NMR (300 MHz, CDCl$_3$) δ3.88 (bs, 2), 7.02–7.11 (m, 2), 7.28–7.53 (m, 3), 7.6714 7.71 (m, 2), 8.13–8.16 (m, 1). $^{13}$C NMR (100 MHz, CDCl$_3$) δ122.57, 122.96, 128.14, 128.38, 128.72, 138.54, 139.86, 139.93, 144.93.

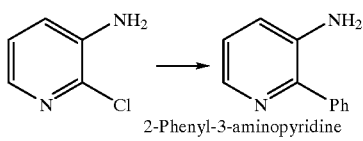

2-Phenyl-3-aminopyridine

A solution of palladium acetate (224.5 mg, 1.00 mmol) and triphenylphosphine (1.05 g, 4.00 mmol) in toluene (1000 mL) was stirred at room temperature for 15 minutes. Phenylboronic acid (114 g, 935 mmol), 2-chloro-3-aminopyridine (100 g, 778 mmol), benzaldehyde (83.4 g, 786 mmol), and toluene (500 mL) were then added followed by a solution of sodium carbonate (200 g, 1.89 mol) in water (1500 mL). The mixture was heated to reflux for 18 hours, cooled to room temperature, and the layers were separated. The organic layer was washed with water (500 mL) and 2.5M aqueous hydrochloric acid was added (630 mL). The aqueous layer was separated and washed with toluene (300 mL). The pH was adjusted to 12—13 using 50% aqueous sodium hydroxide and the mixture was extracted with methyl-tert-butyl ether (500 mL). The organic layer was concentrated and the product was crystallized from diisopropyl ether to afford 2-phenyl-3-aminopyridine (128 g, 97% yield). M. p.=67–68° C. $^1$H NMR (300 MHz, CDCl$_3$) δ3.88 (bs, 2), 7.02–7.11 (m, 2). 7.28–7.53 (m, 3), 7.67–7.71 (m, 2), 8.,13–8.16 (m, 1). $^{13}$C NMR (100 MHz, CDCl$_3$) δ122.57, 122.96, 128.14, 128.38, 128.72, 138.54, 139.86, 139.93, 144.93.

We claim:

1. A process for preparing a compound of formula V or of formula X comprising reacting a compound of the formula

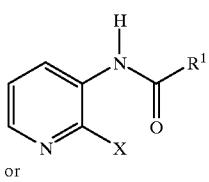

III or

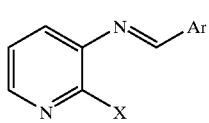

VIII with a compound of the formula

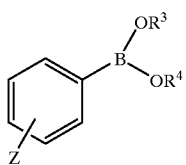

IV in a reaction inert solvent in the presence of a base and a palladium catalyst to obtain a compound of the formula

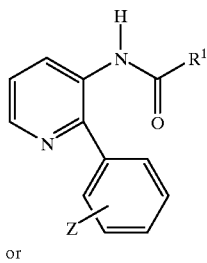

V or

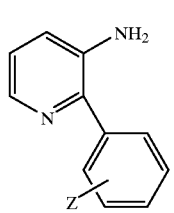

X wherein:

X is Cl, Br, or I;

Z is H, (C$_1$–C$_4$) alkyl, methoxy, tifluoromethoxy, F, or Cl;

Ar is (C$_6$–C$_{10}$) al optionally substituted by from 1 to 3 R$^5$ groups;

R$^1$ is (C$_1$–C$_6$) straight or branched alkyl, (C$_3$–C$_7$) cycloalkyl, or (C$_6$–C$_{10}$) aryl, said alkyl, cycloalkyl, and aryl groups beings optionally substituted by from 1 to 3 R$^5$ groups;

R$^3$ and R$^4$ are independently selected from H, and (C$_1$–C$_6$) alkyl, wherein when R$^3$ and R$^4$ are (C$_1$–C$_6$) alkyl they are optionally linked to each other by a single bond; and each R$^5$ is independently selected from halo, cyano, nitro, (C$_1$–C$_6$) halosubstituted alkyl, (C$_1$–C$_6$) alkoxy, (C$_6$–C$_{10}$)aryloxy, (C$_1$–C$_6$) halosubstituted alkyl, (C$_1$–C$_6$) alkyl, (C$_2$–C$_6$) alkenyl, (C$_2$–C$_6$) alkynyl, (C$_1$–C$_6$) alkylthio, (C$_1$–C$_6$) alkylsulfinyl, (C$_1$–C$_6$) alkylsulfonyl, (C$_1$–C$_6$) alkyl-OC(O)—, (C$_1$–C$_6$) alkyl-OC(O)—(C$_1$–C$_6$) alkyl-, (C$_1$–C$_6$) alkyl-C(O)O—, (C$_1$–C$_6$) alkyl-C(O)—(C$_1$–C$_6$) alkyl(O)—, (C$_1$–C$_6$) alkyl-C(O)—, (C$_1$–C$_6$) alkyl-C(O)—(C$_1$–C$_6$) alkyl-, (C$_6$–C$_{10}$) aryl-, (C$_6$–C$_{10}$) aryl-(C$_1$–C$_6$) alkyl-, and (C$_3$–C$_7$) cycloalkyl.

2. A process according to claim 1 further wherein the compound of formula III or VIII is prepared by reacting a compound of the formula

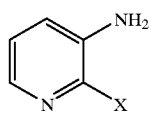

I with a compound of the formula

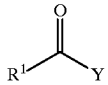

II or

ArCHO  VII in a reaction inert solvent, and wherein:

Y is Cl, Br, I, or —OC(O)R²;

and R² ($C_1$–$C_6$) is straight or branched alkyl, ($C_3$–$C_7$) cycloalkyl, or ($C_6$–$C_{10}$) aryl, said alkyl, cycloalkyl, and aryl groups beings optionally substituted by from 1 to 3 R⁵ groups, wherein said reaction of compound III or VIII with compound IV occurs substantially simultaneously with, or subsequent to, said reaction of compound I with compound II or VII.

3. A process according to claim 1 wherein the compound of formula V is obtained in said process, further comprising deprotecting the compound of formula V in aqueous acid to obtain a salt of compound X.

4. A process according to claim 2 wherein Z is H, R¹ and R² are the same and are independently selected from ($C_1$–$C_6$) straight or branched alkyl, and phenyl, wherein said R¹ and R² are optionally substituted by from 1 to 3 R⁵ groups, R³ and R⁴ are H, and each R⁵ is independently selected from ($C_1$–$C_6$) straight or branched alkyl, phenyl, benzyl, trifluoromethyl, ($C_1$–$C_6$) alkoxy, and trifluoromethoxy.

5. A process according to claim 2 wherein R¹ and R² are methyl.

6. A process according to claim 2 wherein R¹ is methyl and R² is t-butyl.

7. A process according to claim 2 wherein X is Cl and Y is Cl.

8. A process for preparing 2-phenyl-3-aminopyridine comprising (a) reacting a compound of the formula

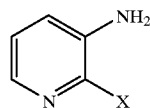  I with a compound of the formula

ArCHO  VII in a reaction inert solvent to obtain a compound of the formula

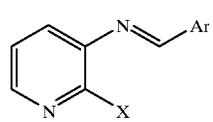  VIII and (b) substantially simultaneously with, or subsequent to step (a), reacting the compound of formula VIII with a compound of the formula

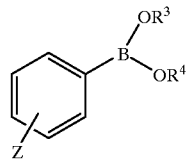  IV in a reaction inert solvent in the presence of a base and a palladium catalyst to obtain a compound of the formula

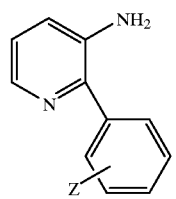  X wherein step (a) is further conducted in the presence of a base where steps (a) and (b) are conducted substantially simultaneously, further wherein:

X is Cl, Br, or I;

Z is H, ($C_1$–$C_4$) alkyl, methoxy, trifluoromethoxy, F or Cl;

Ar is ($C_6$–$C_{10}$) aryl optionally substituted by from 1 to 3 R⁵ groups;

R³ and R⁴ are independently selected from H, and $C_1$–$C_6$ alkyl, wherein when R³ and R⁴ are $C_1$–$C_6$ alkyl they are optionally linked to each other by a single bond; and each R⁵ is independently selected from halo, cyano, nitro, ($C_1$–$C_6$) halosubstituted alkyl, ($C_1$–$C_6$) alkoxy, ($C_6$–$C_{10}$) aryloxy, ($C_1$–$C_6$) halosubstituted alkoxy, ($C_1$–$C_6$) alkyl, ($C_2$–$C_6$) alkenyl, ($C_2$–$C_6$) alkynyl, ($C_1$–$C_6$) alkylthio, ($C_1$–$C_6$) alkylsulfinyl, ($C_1$–$C_6$) alkylsulfonyl, ($C_1$–$C_6$) alkyl-OC(O)—, ($C_1$–$C_6$) alkyl-OC(O)—($C_1$–$C_6$) alkyl-, ($C_1$–$C_6$) alkyl-C(O)O—, ($C_1$–$C_6$) alkyl-C(O)—($C_1$–$C_6$) alkyl-O—, ($C_1$–$C_6$) alkyl-C(O)—, ($C_1$–$C_6$) alkyl-C(O)—, ($C_1$–$C_6$) alkyl-, ($C_6$–$C_{10}$) aryl-, ($C_6$–$C_{10}$) aryl-($C_1$–$C_6$) alkyl-, and ($C_3$–$C_7$) cycloalkyl.

9. A process according to claim 8 wherein steps (a) and (b) are conducted substantially simultaneously.

10. A process according to claim 8 wherein Z is H, R³ and R⁴ are H, and each R⁵ is independently selected from ($C_1$–$C_6$) straight or branched alkyl, phenyl, benzyl, trifluoromethyl, ($C_1$–$C_6$) alkoxy, and trifluoromethoxy, X is Cl, and Ar is phenyl.

* * * * *